United States Patent
Platzek et al.

(10) Patent No.: US 9,447,053 B2
(45) Date of Patent: Sep. 20, 2016

(54) PROCESS FOR THE PREPARATION OF CALCOBUTROL

(75) Inventors: Johannes Platzek, Berlin (DE); Wilhelm Trentmann, Münster (DE)

(73) Assignee: Bayer Intellectual Property GMBH, Monheim (DE)

( * ) Notice: Subject to any disclaimer, the term of this patent is extended or adjusted under 35 U.S.C. 154(b) by 763 days.

(21) Appl. No.: 13/508,198

(22) PCT Filed: Nov. 2, 2010

(86) PCT No.: PCT/EP2010/066655
§ 371 (c)(1),
(2), (4) Date: Aug. 15, 2012

(87) PCT Pub. No.: WO2011/054827
PCT Pub. Date: May 12, 2011

(65) Prior Publication Data
US 2012/0309962 A1    Dec. 6, 2012

(30) Foreign Application Priority Data
Nov. 4, 2009 (DE) .................. 10 2009 053 171

(51) Int. Cl.
*C07D 257/02* (2006.01)
(52) U.S. Cl.
CPC .................. *C07D 257/02* (2013.01)
(58) Field of Classification Search
None
See application file for complete search history.

(56) References Cited

U.S. PATENT DOCUMENTS 5,595,714 A    1/1997  Ripa et al.
2010/0226943 A1*  9/2010  Brennan et al. ............. 424/400

FOREIGN PATENT DOCUMENTS

| CA | 1341176 | 1/2001 |
|----|---------|--------|
| EP | 0270483 | 6/1988 |
| EP | 0448181 | 9/1991 |
| EP | 0596586 | 5/1994 |
| EP | 0643705 | 3/1995 |
| EP | 0743283 | 11/1996 |
| EP | 0986548 | 3/2000 |

OTHER PUBLICATIONS

Platzek. Inorganic Chemistry, 1997, 36(26), 6086-93.*
"Synthesis and Structure of a New Macrocyclic Polyhydroxylated Gadolinium Chelate Use as a Contrast Agent for Magnetic Resonance Imaging" J. Platzek et al. Inorganic Chemistry 1997, vol. 36, pp. 6086-6093.
"Gadovist in Multiple Sclerosis" Karl-Olof Lovblad, Deparment of Neuroradiology, Geneva University Hospital. Touch Briefings 2008.
"The Relationship Between Thermodynamics and the Toxicity of Gadolinium Complexes", William P. Cacheris et al. Magnetic Resonance Imaging, vol. 8, No. 4, 1990.
Product Specification for Gadovist, Gadovist 1.0, 2005.
"Impurity Profiling: Theory and Practice", P. Venkatesan et al./J. Pharm. Sci. & Res. vol. 6(7), 2014, 254-259.
"Diffraction and the X-Ray Powder Diffractometer" B. Fultz et al. Transmission Electron Microscopy and Diffractometry of Materials, Graduate Texts in Physics. Springer-verlag Berlin Heidelberg 2013.
International Search Report and Written Opinion for International Patent Application Publication PCT/EP2010/066655.
E. Toth et al., "Equilibrium and kinetic studies on complexes of 10-[2,3-dihydroxy-(1-hydroxymethyl)-propyl]-1,4,7,10-tetraazacyclododecane-1,4,7-triacetate." Inorganica Chimica Acta 249 (1996) 191-199.

* cited by examiner

*Primary Examiner* — Noble Jarrell
(74) *Attorney, Agent, or Firm* — Joseph L. Kent; David Schramm; James R. Stevenson

(57) ABSTRACT

A process for the preparation of the calcium complex of 10-(2, 3-Dihydroxy-1-(hydroxymethyl)propyl)-1,4,7,10-tetraazacyclodecane-4,7-triacetic acid, also known as Calcobutrol, starting from the pure gadolinium complex (Gadobutrol) is disclosed. Also disclosed is Calcobutrol with a hitherto unknown level of purity.

13 Claims, 1 Drawing Sheet

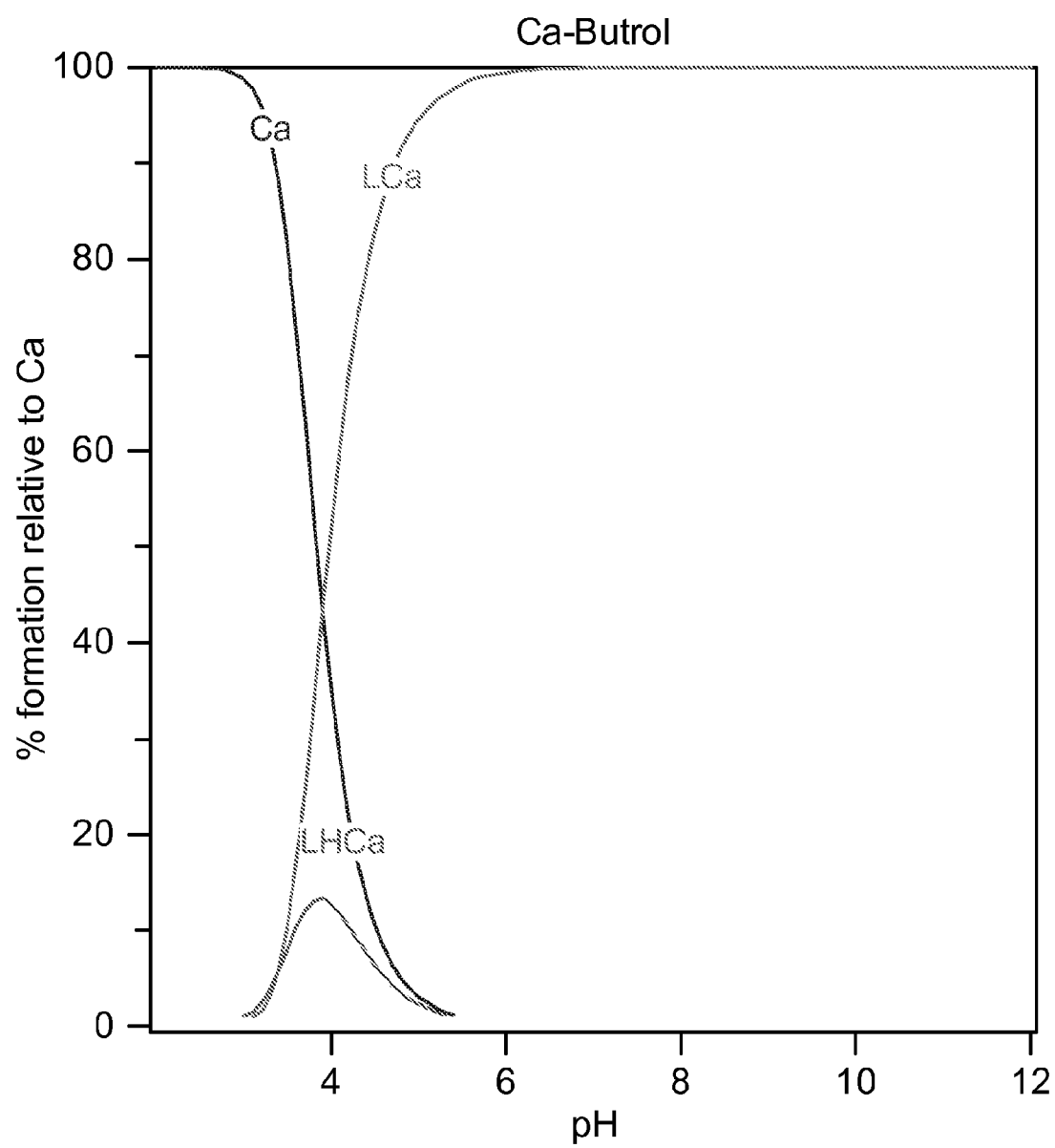

PROCESS FOR THE PREPARATION OF CALCOBUTROL

FIELD OF THE INVENTION

The present invention concerns a process for the preparation of the calcium complex of 10-(2,3-Dihydroxy-1-(hydroxymethyl)propyl)-1,4,7,10-tetraazacyclododecane-1,4,7-triacetic acid, also known as Calcobutrol, and its use for the preparation of galenic formulations. The invention furthermore concerns Calcobutrol with a hitherto unknown level of purity.

BACKGROUND OF THE INVENTION

Calcobutrol is an additive in the galenic formulations of Gadobutrol and solves the problem of preventing the release of free gadolinium in the formulations (solutions). Gadobutrol is a gadolinium-containing contrast agent for nuclear spin tomography and has been allowed in Germany since 2000 as Gadovist® for the indication "contrast enhancement by cranial and spinal magnetic resonance tomography (MRT)" (EP 0 448 181 B1, EP 0 643 705 B1, EP 0 986 548 B1, EP 0 596 586 B1, and CA patent 1341176). Gadobutrol is a non-ionic complex, consisting of gadolinium(III) and the macrocyclic ligand 10-(2,3-Dihydroxy-1-(hydroxymethyl)propyl)-1,4,7,10-tetraazacyclododecane-1,4,7-triacetic acid (butrol). Gadovist is sold as a 1 molar aqueous solution and has the following components in the formulation: Gadobutrol, Calcobutrol sodium salt, Trometamol, hydrochloric acid and water for injection.

It has been found that for most gadolinium-containing contrast agents it is an advantage to apply an excess of the complex-forming ligand in the formulation in the form of the calcium complex (EP 0 270 483 B2). The role of the calcium complex is to prevent the release of free gadolinium in the formulation (e.g. by storage for several years, re-complexation with foreign ions from the glass).

The synthesis of the calcium complex (Calcobutrol) is described in detail in Inorg. Chem. 1997, 36, 6086-6093. The process disclosed therein, however, does not provide Calcobutrol with the purity required by the authorities. An exact reproduction of the process of Scheme 3 (page 6088-6089) results in a material with a purity of only about 94%, as measured by HPLC (stationary phase: Hypersil phenyl (5 μm) from SHANDON; mobile phase: acetonitrile/borate buffer (pH 8) in the vol. ratio 20/100; detection: UV detector (200 nm); injection volume: 10 μl). The ligand available from the synthesis of Gadobutrol (butrol) does not have the required high purity for directly transferring it to the calcium complex. A further purification of the ligand is difficult due to the zwitterionic nature of the ligand. Unlike the ligands BOPTA, DTPA, and DOTA, which crystallise at a pH of 1.7-1.8 (according to U.S. Pat. No. 5,595,714), it is not possible to crystallise butrol at any pH (see comparative Example below) and thus not possible to purify it by crystallisation. Without being bound by a specific theory, the difference in ability to crystallise is ascribed to the dihydroxy-hydroxymethyl-propyl sidechain in butrol, which is not present in any of BOPTA, DTPA, or DOTA. It is likely that the lack of crystallisation is due to a difference in polarity or the ability to form hydrogen bonds. Finally, another possible reason could be the so-called "glycerol effect" from the dihydroxy-hydroxymethyl-propyl sidechain, i.e. the ability of glycerol to prevent crystallisation of water at 0° C., disrupting hydrogen bonds in the water crystals.

While the neutral gadolinium complex (Gadobutrol) can be purified in an ion exchange column (such as Amberlite IRC 50, Amberlite FPC3500, or Amberlite IRA 67) and subsequently obtained in very high purity (>99.7%) through a very efficient crystallisation (e.g. from ethanol, preferably with less than 200 ppm water), this is not possible for Calcobutrol because of the extra acid functionality. A purification of the calcium complex was unsuccessful since even by preparative HPLC there was an impurity very close to the main peak that could not be separated. Several different ways of separating Calcobutrol by HPLC were attempted (varying mobile phases, gradients etc.), but none of them accomplished the separation.

The thermodynamic stability constant of Calcobutrol and the acid dissociation constant have been determined by pH-potentiometric equilibrium titrations of the ligand (butrol) in the presence of $Ca^{2+}$ ions (at 25° C., in 0.1 N KCl) at different ratios of $Ca^{2+}$:ligand. The results are:

$$\log(K_{CaL^-}) = 14.67 \pm 0.02 \quad K_{CaL^-} = [CaL^-]/[Ca^{2+}][L^{3-}]$$

$$pK_a = 3.39 \pm 0.12 \quad K_a = [CaL^-][H^+]/[CaLH]$$

Based on these measured values, the distribution of calcium between free calcium ion, neutral complex (Calcobutrol, ligand has two negative charges), and anionic complex (ligand has three negative charges) can be calculated for different pH values. The result is presented in FIG. 1. It is evident that the neutral complex does not constitute more than 20% of the calcium-containing species at any pH. Due to this equilibrium between the calcium-containing species, preparative methods in aqueous solution will lead to some impurities.

While the anionic complex is the dominant species at higher pH values, this is not very useful for purification purposes. The salts with this complex (e.g. the sodium salt) are not suitable for work-up. The sodium salt of the complex is a highly hygroscopic, glassy material, which cannot be handled at any useful scale. In the preparation of the Gadovist solution, the sodium salt is therefore prepared in situ by adding sodium hydroxide to Calcobutrol.

The large difference in stability between Gadobutrol and Calcobutrol is what makes Calcobutrol useful in the Gadovist formulation in the first place, i.e. the large difference in stability between the gadolinium complex and the calcium complex means that the calcium complex will scavenge any free gadolinium ions by forming the gadolinium complex.

It is an object of the present invention to obtain very pure Calcobutrol in the highest possible yield, preferably in crystalline form.

BRIEF DESCRIPTION OF FIGURES

FIG. 1 shows the distribution of calcium-containing species as a function of pH for the Calcobutrol complex and associated compounds.

DETAILED DESCRIPTION OF THE INVENTION

It has surprisingly been found that it is possible to prepare Calcobutrol efficiently by starting from very pure Gadobutrol. The gadolinium is removed by de-complexation from the complex Gadobutrol to obtain the ligand with a high purity, which subsequently is complexed with $Ca^{2+}$ ions.

The de-complexation of gadolinium complexes with oxalic acid by addition of a mineral acid (preferably hydrochloric acid) is described in the literature for ligands different from butrol. It is disclosed in U.S. Pat. No. 5,595,714 how gadolinium as well as the free ligand can be regained through de-complexation with oxalic acid/hydrochloric acid from the gadolinium-containing contrast agent. The use of the process for preparing calcium salts is not disclosed in U.S. Pat. No. 5,595,714.

The present invention concerns a process for the preparation of the calcium complex of 10-(2,3-Dihydroxy-1-(hydroxymethyl)propyl)-1,4,7,10-tetraazacyclodecane-1,4,7-triacetic acid (Calcobutrol), wherein a) the gadolinium complex of 10-(2,3-Dihydroxy-1-(hydroxymethyl)propyl)-1,4,7,10-tetraazacyclodecane-1,4,7-triacetic acid (Gadobutrol) is de-complexed with a de-complexing agent,
b) the precipitated gadolinium salt is removed,
c) the free ligand in the solution resulting from b) is bound to an acidic ion exchange resin,
d) said resin is eluted with an aqueous alkaline solution,
e) the eluate is treated with acidic ion exchange resin, and
f) the ligand is complexed with $Ca^{2+}$ ions and crystallised.

The term "de-complexing agent" in the context of the present invention is intended to mean a reagent capable of forming Gd salts which are only slightly soluble in water. Examples of de-complexing reagents are oxalate ion sources, such as oxalic acid, and phosphate ion sources, such as phosphoric acid, which form the insoluble gadolinium oxalate and gadolinium phosphate salts, respectively. Preferred de-complexing agents are oxalic acid and phosphoric acid, most preferred oxalic acid.

The de-complexation works particularly well in water at temperatures from 75 to 100° C., such as from 80 to 95° C., for example from 87.5 to 92.5° C., preferably at about 90° C.

After the release of the ligand (butrol) follows the treatment with acidic ion exchange resin, especially at a pH value of 3.65 to 3.80, preferably at about 3.72. Amberlite 252 C or Amberlite IR 120 are examples of useful ion exchange resins.

Preferred aqueous alkaline reagents for the eluent are bases that may be removed from an aqueous solution by distillation. The advantage of such reagents is that they will be removed from the ligand-containing eluate by evaporation of water. The aqueous alkaline reagents may be ammonia or volatile amines. In the present context, the term "volatile amine" is intended to mean any primary, secondary or tertiary aliphatic amine independently with 1 to 4 carbon atoms in the alkyl chain bonded to the central nitrogen atom and which has a boiling point at atmospheric pressure at 95° C. or less, such as at 80° C. or less, 70° C. or less, 60° C. or less, 50° C. or less, 40° C. or less, preferably at 30° C. or less or at 15° C. or less. Examples of volatile amines are methylamine, ethylamine, n-propylamine, isopropylamine, dimethylamine, diethylamine, triethylamine, trimethylamine, di-n-propylamine, di-isopropylamine, n-butylamine, sec-butylamine, 1-amino-2,2-dimethylpropane, 2-amino-2-methylbutane, 2-amino-3-methylbutane, 2-aminopentane, and 3-aminopentane. In a presently preferred embodiment, the alkaline reagent for the eluent is ammonia, dimethylamine, methylamine, ethylamine, trimethylamine, iso-propylamine, or mixtures thereof, more preferred ammonia or dimethylamine, or mixtures thereof, most preferred is ammonia.

In one embodiment, the free ligand is complexed with $Ca^{2+}$ ions directly after treating with the ion exchange resin, i.e. without isolating the ligand first. In another embodiment, the free ligand is first isolated by freeze-drying before complexation with $Ca^{2+}$ ions.

Calcium carbonate, oxide, or hydroxide are preferred sources of $Ca^{2+}$ ions for complexation. Said complexation is preferably carried out in aqueous solution at temperatures from 75 to 100° C., such as from 80 to 95° C., for example from 87.5 to 92.5° C., preferably at about 90° C.

It was surprisingly found that the addition of mineral acid, as described in U.S. Pat. No. 5,595,714, is not necessary for de-complexation. If highly pure Gadobutrol is reacted directly in water with a stoichiometric amount of de-complexing agent, such as oxalic acid, a colourless solution of butrol in water of excellent quality and purity after quantitative de-complexation and filtering off of gadolinium oxalate is obtained. Thus, in one embodiment, the de-complexing agent, such as oxalic acid, is added to Gadobutrol at a pH higher than 2, such as at a pH higher than 3, e.g. a pH higher than 4, preferably a pH higher than 4.5. The Calcobutrol complex may be prepared directly from the butrol solution after a further purification step.

To assure that no free gadolinium is present in the butrol solution, it is put through an ion exchange treatment. To remove any residual ions the butrol solution is placed on an ion exchange column and washed thoroughly with water. Subsequently, the ligand is eluted with an aqueous alkaline reagent, such as ammonia-water, and the aqueous eluate solution is evaporated gently under vacuum. The residue is diluted with water. After treatment with active carbon the pH value is set to 3.7 by addition of acidic ion exchange resin. The exchange resin is filtered off and the solution is subsequently freeze-dried.

Phosphoric acid may be used instead of oxalic acid. In this case, gadolinium phosphate ($GdPO_4$) precipitates. The ligand may be worked up in an analogous manner.

It is in principle possible to continue directly and perform the complexation with a calcium salt. It has been found, however, that it is possible to isolate the ligand through gentle freeze-drying, a convenient storage form being obtained in this way.

The final reaction to Calcobutrol is carried out by complexing butrol with a stoichiometric amount of calcium carbonate in water with heating. CaO and $Ca(OH)_2$ may, however, also be used.

To remove particles and nuclei treatment with active carbon and subsequent filtration is used. The filtrate is evaporated in vacuum as much as possible and is brought to crystallisation through addition of ethanol. For this, heating with reflux and subsequent cooling is applied. The precipitated crystalline product is filtered off and washed with a little bit of ethanol. Subsequently, it is dried at 70° C. in a vacuum chamber. It has been found that crystallisation may also be made from acetone or isopropanol, ethanol however being the preferred solvent.

Without being bound by a particular theory, it has been found that the crystallisation of Calcobutrol in ethanol or other suitable solvents drives the equilibrium in aqueous solution between free calcium ions and ligands on the one hand and the Calcobutrol complex on the other hand (illustrated in FIG. 1) towards the stable, crystallised complex. Thus, at stoichiometric amounts of calcium ions and butrol at the beginning of the complexation step only the complex remains after crystallisation. It has however also been found that pure butrol must be used for the complexation process to result in pure Calcobutrol. If the butrol is not pure, the Calcobutrol will contain a similar level of impurities. This was observed for the process according to Inorg. Chem. 1997, 36, 6086-6093.

In one embodiment, the invention concerns a process, wherein the gadolinium complex of 10-(2,3-Dihydroxy-1-(hydroxymethyl)propyl)-1,4,7,10-tetraazacyclodecane-1,4,7-triacetic (Gadobutrol) acid is de-complexed with oxalic acid or phosphoric acid in water with heating, the precipitated gadolinium oxalate/phosphate is filtered off, the free ligand is bound to an acidic ion exchange resin, the resin is eluted with an aqueous ammonia solution, after evaporation of the solution pH is set to 3.6-3.8 with acidic ion exchange resin, the solution is freeze-dried, the ligand is complexed with $Ca^{2+}$ ions with heating, the complex is crystallised from ethanol after complete reaction, and after isolation the crystals are dried under vacuum.

The Calcobutrol prepared in this manner is characterised by a very high quality. The product is colourless and soluble in water and has a purity of 99.0% or more, in some batches of 99.4% or more (purity according to HPLC, 100% method). The whole process, from Gadobutrol to Calcobutrol, is characterised by a high reproducibility and workability. The total yield of 91.2% is very good. The product is stable for storage and may be used for the formulation of Gadovist solutions. The sodium salt of Calcobutrol is obtained through addition of a stoichiometric amount of sodium hydroxide in situ. Gadovist solutions prepared in this manner are stable for several years and provide the security that toxic gadolinium will never be released into the solution.

It has thus been achieved to meet the wishes of authorities and practitioners, to provide Calcobutrol with high purity at a low cost, which may be used directly for further processing and preparation of Gadovist.

The invention also concerns the use of the calcium complex's 10-(2,3-Dihydroxy-1-(hydroxymethyl)propyl)-1,4,7,10-tetraazacyclodecane-1,4,7-triacetic acid for the preparation of commercial galenic formulations of Gadobutrol.

EXAMPLES

HPLC, 100% Method

Stationary phase: Hypersil ODS, 3 μm, or equivalent packing material 125×4.6 mm
Mobile Phase:
Eluent A: Prepare a solution with 2.0 g per liter octanesulfonic acid sodium salt monohydrate in water. Adjust the pH value to 2.0±0.1 with sulphuric acid.
Eluent B: Acetonitrile for chromatography
Gradient Schedule:

| Time [min] | Eluent A [vol %] | Eluent B [vol %] |
|---|---|---|
| 0 | 87 | 13 |
| 20 | 87 | 13 |
| 45 | 70 | 30 |
| 50 | 70 | 30 |
| 51 | 87 | 13 |
| 60 | 87 | 13 |

Flow rate: 1.0 ml/min
UV detection wavelength: 197 nm
Sample concentration: 7 mg/1 ml eluent A
Injection volume: 10 μl

Comparative Example

It is not possible to use the process disclosed in U.S. Pat. No. 5,595,714 for the preparation of Calcobutrol. Gadobutrol is, as described in the US patent, stirred with hydrochloric acid and then oxalic acid in water (pH 0.8) at 20° C. for about 6 h., and the precipitated gadolinium oxalate is filtered off. The filtrate is divided into several portions and the pH value is adjusted by addition of 20% aqueous sodium hydroxide. Since it is unknown at which pH the ligand would crystallise, several solutions, each with a pH difference of 0.1, are tested. The result of the crystallisation experiments is provided in the following table:

| pH value | After 24 h | After 1 week | After 1 month |
|---|---|---|---|
| 0.8 | No crystals | No crystals | No crystals |
| 0.9 | No crystals | No crystals | No crystals |
| 1.0 | No crystals | No crystals | No crystals |
| 1.1 | No crystals | No crystals | No crystals |
| 1.2 | No crystals | No crystals | No crystals |
| 1.3 | No crystals | No crystals | No crystals |
| 1.4 | No crystals | No crystals | No crystals |
| 1.5 | No crystals | No crystals | No crystals |
| 1.6 | No crystals | No crystals | No crystals |
| 1.7 | No crystals | No crystals | No crystals |
| 1.8 | No crystals | No crystals | No crystals |
| 1.9 | No crystals | No crystals | No crystals |
| 2.0 | No crystals | No crystals | No crystals |
| 2.1 | No crystals | No crystals | No crystals |
| 2.2 | No crystals | No crystals | No crystals |
| 2.3 | No crystals | No crystals | No crystals |
| 2.4 | No crystals | No crystals | No crystals |
| 2.5 | No crystals | No crystals | No crystals |
| 2.6 | No crystals | No crystals | No crystals |
| 2.7 | No crystals | No crystals | No crystals |
| 2.8 | No crystals | No crystals | No crystals |
| 2.9 | No crystals | No crystals | No crystals |
| 3.0 | No crystals | No crystals | No crystals |
| 3.1 | No crystals | No crystals | No crystals |
| 3.2 | No crystals | No crystals | No crystals |
| 3.3 | No crystals | No crystals | No crystals |
| 3.4 | No crystals | No crystals | No crystals |
| 3.5 | No crystals | No crystals | No crystals |
| 3.6 | No crystals | No crystals | No crystals |
| 3.7 | No crystals | No crystals | No crystals |
| 3.8 | No crystals | No crystals | No crystals |
| 3.9 | No crystals | No crystals | No crystals |
| 4.0 | No crystals | No crystals | No crystals |

It has not been successful trying to crystallise the ligand according to the teaching of the US patent. HPLC studies show that under the strongly acidic conditions the appearance of new impurities are observed, which lead to a decrease in the quality of the ligand. It is furthermore observed that the originally colourless ligand turns yellow after 6 hours and the impurity can not be removed. The method from the US patent described above is thus unsuitable for the preparation of Calcobutrol since the further work-up of this ligand only results in coloured Calcobutrol with 93% purity (HPLC, 100% method).

It has surprisingly been shown, however, that isolation via crystallisation is not necessary. Conditions have been found that are so gentle that it is possible to remove gadolinium from the complex, so that the highly pure ligand in solution may be reacted directly or isolated by freeze-drying.

Example 1

Preparation of Butrol 26.255 kg of Gadobutrol (water content 4.78%, purity >99% assured by ion exchange and crystallisation) and 10.108 kg of oxalic acid dihydrate (solid, 99%) are poured in a container with a stirrer, 175 liters of demineralised water are added and the mixture is stirred at 90° C. for 5 hours. The mixture is cooled to 20° C. (pH measurement gives values from 3.1 to 3.5). The precipitated gadolinium oxalate is siphoned and washed twice with 50 l of water. The filtrate is put on a cation exchange column, filled with 250 l of Amberlite 252 C, and then the column is washed with water.

The product is eluted with a mixture of 250 l demineralised water and 125 l of 25% ammonia from the column and collected in 13 fractions.

| Eluate fraction | Volume in l | pH | TLC finding[1] |
|---|---|---|---|
| 1 | 50 | 4.4 | No product |
| 2 | 50 | 4.6 | No product |
| 3 | 45 | 4.4 | No product |
| 4 | 45 | 3.9 | No product |
| 5 | 20 | 3.6 | Product |
| 6 | 30 | 3.7 | Product |
| 7 | 40 | 3.7 | Product |
| 8 | 25 | 4.9 | Product |
| 9 | 20 | 5.4 | Product |
| 10 | 45 | 10.9 | Product |
| 11 | 50 | 12.2 | No product |
| 12 | 50 | 12.3 | No product |
| 13 | 100 | 2.3 | No product |

[1] It is decided by TLC (Thin-layer chromatography) whether a fraction contains product.

Eluate fractions 5 to 10 are evaporated on a rotary evaporator at 70° C. bath temperature in vacuum to approximately 35 l. The pH value of the concentrate is 6.7.

The oily residue is taken up in 125 l of demineralised water and 3.75 kg of active carbon (Norit SX PLUS, first washed thoroughly with water) are added, and the solution is then heated to 90° C. inner temperature for 1 hour. The warm solution is filtered to remove the active carbon and the carbon is washed three times with 25 l of 70° C. water each time.

The mixture is cooled to 20° C., the pH is adjusted to pH 3.72 by addition of acidic ion exchange resin (Amberlite IR 120, the resin is added in portions of 6.5 l—a total of 45.5 l; a 100 ml probe was taken—additional resin did not change the pH). The ion exchange resin is filtered off and washed 4 times with 25 l of demineralised water each time. The filtrate together with the washing water is evaporated in a heating stirrer at 70° C. under vacuum to a volume of approximately 100 l. The solution is cooled to 20° C. and subsequently freeze-dried in a freeze-drier.

Yield: 18.15 kg (17.69 kg=95% theoretical, adjusted for water) colourless amorphous powder.

Water contents (Karl-Fischer): 2.60%
Elementary Analysis (Corrected for Water):

| Element | C | H | N | O |
|---|---|---|---|---|
| Calculated | 47.99 | 7.61 | 12.44 | 31.96 |
| Found | 47.77 | 7.73 | 12.38 | 32.04 |

HPLC purity (100% method): >99%

Example 2

Preparation of Calcobutrol

A total of 3.356 kg calcium carbonate (99.3%) is added in portions to 15.39 kg butrol (water contents: 2.6%) dissolved in 120 l demineralised water and it is stirred for one hour at 90° C. inner temperature. It is subsequently cooled to 20° C. and 1.5 kg active carbon (Norit SX PLUS; the carbon is first washed thoroughly with water) is added. It is stirred for one hour at 20° C. and the carbon is subsequently filtered off. The carbon is washed three times with 15 l of water each time.

Subsequently, the filtrate together with the washing water is evaporated in a heating stirrer at 80° C. under vacuum to an oil, which can still be stirred and corresponds to 1.4 times the original butrol. 150 l of ethanol is added to the oil and it is subsequently boiled under reflux for 3 hours. It is cooled to 20° C. and the precipitated crystal suspension is filtered off. The crystals are washed twice with 15 l ethanol each time.

The product, still moist from ethanol, is dried in a vacuum dryer set to 70° C. until the weight is constant.

Yield: 16.27 kg (96% theoretical) colourless crystals
Elementary Analysis:

| Element | C | H | N | O | Ca |
|---|---|---|---|---|---|
| Calculated | 44.34 | 6.41 | 11.49 | 29.53 | 8.22 |
| Found | 44.54 | 6.57 | 11.34 | 29.43 | 8.17 |

HPLC purity (100% method): >99.0%

Experiments on a laboratory scale corresponding to this example were conducted with acetone and isopropanol instead of ethanol as the solvent for crystallisation. Similar purities were obtained.

The invention claimed is:

1. A process for the preparation of a calcium complex of 10-(2,3-Dihydroxy-1-(hydroxymethyl)propyl)-1,4,7,10-tetraazacyclododecane-1,4,7-triacetic acid comprising:
   a) de-complexing a gadolinium complex of 10-(2,3-Dihydroxy-1-(hydroxymethyl)propyl)-1,4,7,10-tetraazacyclododecane-1,4,7-triacetic acid with a de-complexing agent to give a solution of a free ligand and a precipitated gadolinium salt,
   b) removing the precipitated gadolinium salt,
   c) binding the free ligand in the solution resulting from step b) to an acidic ion exchange resin,
   d) eluting the acidic ion exchange resin with an aqueous alkaline solution to give an eluate comprising the free ligand,
   e) treating the eluate with a second acidic ion exchange resin to acidify the eluate comprising the free ligand, and
   f) complexing the free ligand with $Ca^{2+}$ ions from a calcium ion source to give a resulting calcium complex, and crystallizing the resulting calcium complex to give a crystallized calcium complex.

2. The process according to claim 1, wherein the de-complexing agent in step a) is an oxalate ion source or a phosphate ion source.

3. The process according to claim 2, wherein the de-complexing agent in step a) is oxalic acid.

4. The process according to claim 1, wherein the de-complexation reaction according to step a) is carried out in water at temperatures from 75 to 100° C.

5. The process according to claim 1, wherein the aqueous alkaline solution of step d) is a solution of ammonia or a volatile amine, or mixtures thereof.

6. The process according to claim 5, wherein the aqueous alkaline solution in step d) is a solution of ammonia, dimethylamine, methylamine, ethylamine, trimethylamine, iso-propylamine, or mixtures thereof.

7. The process according to claim 6, wherein the aqueous alkaline solution in step d) is a solution of ammonia.

8. The process according to claim 1, wherein the free ligand resulting from step e) is isolated by freeze-drying.

9. The process according to claim 1, wherein the free ligand resulting from step e) is reacted directly with the calcium ion source without isolating the free ligand first.

10. The process according to claim 1, wherein the calcium ion source in step f) is calcium carbonate, calcium oxide, or calcium hydroxide.

11. The process according to claim 1, wherein a pH in step a) before adding the de-complexing agent is higher than 2.

12. The process according to claim 1, wherein the crystallized calcium complex is the calcium complex of 10-(2,3-Dihydroxy-1-(hydroxymethyl)propyl)-1,4,7,10-tetraazacyclodecane-1,4,7-triacetic acid having a purity of 99.0% or more.

13. The process according to claim 1, wherein the crystallized calcium complex is the calcium complex of 10-(2,3-Dihydroxy-1-(hydroxymethyl)propyl)-1,4,7,10-tetraazacyclodecane-1,4,7-triacetic acid having a purity of 99.4% or more.

* * * * *

UNITED STATES PATENT AND TRADEMARK OFFICE
CERTIFICATE OF CORRECTION

PATENT NO. : 9,447,053 B2
APPLICATION NO. : 13/508198
DATED : September 20, 2016
INVENTOR(S) : Platzek and Trentmann Page 1 of 2

It is certified that error appears in the above-identified patent and that said Letters Patent is hereby corrected as shown below:

On the Title Page

In the Abstract (57), Lines 2-3, delete "10-(2,3-Dihydroxy-1-(hydroxymethyl)propyl)-1,4,7,10-tetraazacyclodecane-4,7-triacetic acid", and insert -- 10-(2,3-Dihydroxy-1-(hydroxymethyl)propyl)-1,4,7,10-tetraazacyclododecane-1,4,7-triacetic acid --, therefor.

In the Specification

In Column 1, Lines 7-9, delete "10-(2,3-Dihydroxy-1-(hydroxymethyl)propyl)-1,4,7,10-tetraazacyclodecane-1,4,7-triacetic acid", and insert -- 10-(2,3-Dihydroxy-1-(hydroxymethylpropyl)-1,4,7,10-tetraazacyclododecane-1,4,7-triacetic acid --, therefor.

In Column 1, Lines 26-28, delete "10-(2,3-Dihydroxy-1-(hydroxymethyl)propyl)-1,4,7,10-tetraazacyclodecane-1,4,7-triacetic acid", and insert -- 10-(2,3-Dihydroxy-1-(hydroxymethylpropyl)-1,4,7,10-tetraazacyclododecane-1,4,7-triacetic acid --, therefor.

In Column 3, Lines 9-11, delete "10-(2,3-Dihydroxy-1-(hydroxymethyl)propyl)-1,4,7,10-tetraazacyclodecane-1,4,7-triacetic acid", and insert -- 10-(2,3-Dihydroxy-1-(hydroxymethylpropyl)-1,4,7,10-tetraazacyclododecane-1,4,7-triacetic acid --, therefor.

In Column 3, Lines 12-14, delete "10-(2,3-Dihydroxy-1-(hydroxymethyl)propyl)-1,4,7,10-tetraazacyclodecane-1,4,7-triacetic acid", and insert -- 10-(2,3-Dihydroxy-1-(hydroxymethylpropyl)-1,4,7,10-tetraazacyclododecane-1,4,7-triacetic acid --, therefor.

In Column 5, Lines 2-4, delete "10-(2,3-Dihydroxy-1-(hydroxymethyl)propyl)-1,4,7,10-tetraazacyclodecane-1,4,7-triacetic (Gadobutrol) acid", and insert -- 10-(2,3-Dihydroxy-1-(hydroxymethyl)propyl)-1,4,7,10-tetraazacyclododecane-1,4,7-triacetic acid (Gadobutrol) --, therefor.

Signed and Sealed this
Twentieth Day of November, 2018

Andrei Iancu
*Director of the United States Patent and Trademark Office*

CERTIFICATE OF CORRECTION (continued)
U.S. Pat. No. 9,447,053 B2

In Column 5, Lines 32-33, delete "10-(2,3-Dihydroxy-1-(hydroxymethyl)propyl)-1,4,7,10-tetraazacyclodecane-1,4,7-triacetic acid", and insert -- 10-(2,3-Dihydroxy-1-(hydroxymethylpropyl)-1,4,7,10-tetraazacyclododecane-1,4,7-triacetic acid --, therefor.

In the Claims

In Column 8, Lines 31-32 in Claim 1, delete "10-(2,3-Dihydroxy-1-(hydroxymethyl)propyl)-1,4,7,10-tetraazacyclodecane-1,4,7-triacetic acid", and insert -- 10-(2,3-Dihydroxy-1-(hydroxymethyl)propyl)-1,4,7,10-tetraazacyclododecane-1,4,7-triacetic acid --, therefor.

In Column 8, Lines 33-35 in Claim 1, delete "10-(2,3-Dihydroxy-1-(hydroxymethyl)propyl)-1,4,7,10-tetraazacyclodecane-1,4,7-triacetic acid", and insert -- 10-(2,3-Dihydroxy-1-(hydroxymethyl)propyl)-1,4,7,10-tetraazacyclododecane-1,4,7-triacetic acid --, therefor.

In Column 9, Lines 12-14 in Claim 12, delete "10-(2,3-Dihydroxy-1-(hydroxymethyl)propyl)-1,4,7,10-tetraazacyclodecane-1,4,7-triacetic acid", and insert -- 10-(2,3-Dihydroxy-1-(hydroxymethyl)propyl)-1,4,7,10-tetraazacyclododecane-1,4,7-triacetic acid --, therefor.

In Column 9, Lines 17-19 in Claim 13, delete "10-(2,3-Dihydroxy-1-(hydroxymethyl)propyl)-1,4,7,10-tetraazacyclodecane-1,4,7-triacetic acid", and insert -- 10-(2,3-Dihydroxy-1-(hydroxymethyl)propyl)-1,4,7,10-tetraazacyclododecane-1,4,7-triacetic acid --, therefor.